United States Patent [19]
Sinn et al.

[11] Patent Number: 6,147,207
[45] Date of Patent: Nov. 14, 2000

[54] METHOD FOR PRODUCING CHLORINS AND BACTERIOCHLORINS CONTAINING POLYETHER

[75] Inventors: Hannsjörg Sinn, Wiesloch; Hans-Hermann Schrenk, Zeiskam; Michael Kaus, Heidelberg; Wolfgang Maier-Borst, Dossenheim; Gerd Stehle, Heidelberg, all of Germany

[73] Assignee: Deutsches Krebsforschungszentrum Stiftung des Offentlichen, Heidelberg, Germany

[21] Appl. No.: 09/214,362

[22] PCT Filed: Jul. 4, 1997

[86] PCT No.: PCT/DE97/01438

§ 371 Date: Mar. 22, 1999

§ 102(e) Date: Mar. 22, 1999

[87] PCT Pub. No.: WO98/01156

PCT Pub. Date: Jan. 15, 1998

[30] Foreign Application Priority Data

Jul. 5, 1996 [DE] Germany .......................... 196 27 164

[51] Int. Cl.⁷ .................... C07D 487/22; A61K 31/40
[52] U.S. Cl. ................... 540/145; 514/183; 514/410
[58] Field of Search ........................ 540/145; 514/183, 514/410

[56] References Cited

U.S. PATENT DOCUMENTS 5,238,940  8/1993  Liu et al. ................................ 514/410
5,284,831  2/1994  Kahl et al. .............................. 514/21

FOREIGN PATENT DOCUMENTS 40 17 439 A1  12/1991  Germany .
WO 95/29915   of 1995  WIPO .
WO 95 10522   4/1995   WIPO .
WO 95 29915   11/1995  WIPO .

OTHER PUBLICATIONS

Whitlock, Jr. et al. "Diimide Reduction of Porphyrins," Journal of the American Chemical Society. XP–002053835. Dec. 17, 1969, pp. 7485–7489.

*Primary Examiner*—Mukund J. Shah
*Assistant Examiner*—Pavanaram K Sripada
*Attorney, Agent, or Firm*—Steven J. Hultquist; William A. Barrett

[57] ABSTRACT

This invention relates to a process for the preparation of polyether-including chlorins and/or bacteriochlorins, comprising the following steps:

(a) bonding a polyether to a porphyrin and
(b) reacting the polyether-including porphyrin with a reducing agent.

Furthermore, this invention concerns the polyether-including chlorins and bacteriochlorins, obtained by the process, as well as the use thereof for the photodynamic treatment of tumors.

12 Claims, 4 Drawing Sheets

METHOD FOR PRODUCING CHLORINS AND BACTERIOCHLORINS CONTAINING POLYETHER

This application is a 371 of PCT/DE97/01438.

The present invention relates to a process for the preparation of polyether-including chlorins and bacteriochlorins, compounds as such and their use.

It is known to use polyether-including chlorins and bacteriochlorins for treating tumors in the photodynamic therapy. They are prepared by initially synthesizing chlorins and bacteriochlorins from porphyrins. Following isolation and purification, polyethers are bound to the chlorins and bacteriochlorins. The resulting polyether-including chlorins and bacteriochlorins are then isolated and purified. The multiple isolation and purification steps render the process very complicated and expensive. In addition, the polyether-including chlorins and bacteriochlorins may only be prepared in small amounts and poor yield.

Therefore, it is the object of the present invention to provide a process by which polyether-including chlorins and bacteriochlorins can be prepared with the above drawbacks.

According to the invention this is achieved by the subject matters defined in the claims.

Thus, the subject matter of the present invention relates to a process for the preparation of polyether-including chlorins and/or bacteriochlorins, which comprises the following steps:

(a) binding a polyether to a porphyrin and (b) reacting the polyether-including porphyrin with a reducing agent.

The expression "porphyrin" comprises compounds of any kind having the macrocyclic tetrapyrrole skeleton. Representatives of these compounds are porphyrins which have one or more, preferably 4, functional groups, e.g. acid groups such as carboxylic acid and/or sulfonic acid groups. Examples thereof are o-, m- and/or p-tetracarboxyphenylporphin (TCCP) and o-, m- and/or p-tetrasulfophenylporphin. It is favorable for the porphyrin to be activated with the polyether prior to its reaction. Such an activation may be e.g. the conversion of the above acid groups into a more reactive derivative, e.g. acid halide such as acid chloride or bromide.

In step (a) of the process according to the invention, a polyether is bound to the porphyrin so as to obtain a polyether-including porphyrin. The bond may be covalent. For example, the polyether may be bound to functional groups of the porphyrin. The polyether preferably has a molecular weight of 100 to 20,000 daltons, more preferably 2,000 to 5,000 daltons and most preferably about 5,000 daltons. In addition, the polyether may be etherified or esterified at the terminal hydroxyl group with a $C_1$–$C_{12}$ alkyl group, particularly methyl group. Representatives of the polyethers are polyethylene glycols such as methoxypolyethylene glycol and amino-Ω-methoxypolyethylene glycol (aminoPEG). Several polyethers, preferably four, may be bound to the porphyrin. The polyethers may be identical or differ from one another. If several polyethers are bound to the porphyrin, the sum of the molecular weight of the polyethers is preferably from 8,000 to 50,000 daltons.

In step (b) of the process according to the invention, the polyether-including porphyrin of step (a) is reacted by means of a reducing agent. For this purpose, the porphyrin needs not be either isolated or purified. Therefore, steps (a) and (b) can be carried out in a one-pot reaction. Every agent which can effect a reduction of the porphyrin to form a chlorin, i.e. dihydroporphyrin, particularly 7,8-dihydroporphyrin, and/or bacteriochlorin, i.e. tetrahydroporphyrin, particularly 7,8,17,18-tetrahydroporphyrin, is suitable as reducing agent. Examples of such reducing agents are hydrazides such as toluenesulfonic acid hydrazide.

Steps (a) and (b) of the process according to the invention are preferably carried out in an organic, polar solvent miscible with water, e.g. dioxan or a mixture of dioxan and ethylene triamine. The advantage of this is e.g. that water or aqueous solutions may be added and an ultrafiltration may be carried out for separating undesired accompanying substances.

Following step (b) of the process according to the invention, the reaction batch has polyether-including chlorins and/or bacteriochlorins. The composition of the reaction batch depends on the reducing agent, its amount and reaction time. This may be determined as usual.

It is preferred to carry out an isolation step after step (b) of the process according to the invention, which may comprise the addition of the reaction batch to water, e.g. bidistilled water, buffer or a weakly reducing aqueous medium such as a sodium-ascorbate solution as well as the subsequent ultrafiltration. Polyether-including chlorins are stable in water. In contrast thereto, polyether-including bacteriochlorins are autoxidized in water to give the corresponding polyether-including chlorins. In this way, polyether-including bacteriochlorin formed can be converted into the corresponding chlorin. In a weakly reducing, aqueous medium both polyether-including chlorins and polyether-including bacteriochlorins are stable. Unwanted accompanying substances, e.g. unreacted polyethers, may be separated by ultrafiltration. Ultrafiltration has the advantage that it can be carried out easily. The separation of a mixture of polyether-including chlorins and bacteriochlorins, present after the ultrafiltration, may take place as usual, e.g. by chromatographic processes.

A preferred process according to the invention is shown in FIGS. 1A–1D.

The process according to the invention distinguishes itself in that it requires little time, material and labor. In addition, the reactions proceed virtually quantitatively, so that the polyether-including chlorins and bacteriochlorins can be produced almost without loss, i.e. in high yields, from the porphyrins. Furthermore, the polyether-including chlorins and bacteriochlorins are already available in a tumor-penetrating form and may be provided before long in a form ready for application. Thus, the process according to the invention is suited in the best possible manner for the preparation of polyether-including chlorins and bacteriochlorins which can be used for the photodynamic treatment of tumors.

Polyether-including chlorins and bacteriochlorins prepared according to the invention also represent a subject matter of the present invention.

The invention is elucidated by the example:

EXAMPLE

Preparation of polyether-including chlorin and bacteriochlorin

Figure 1A:
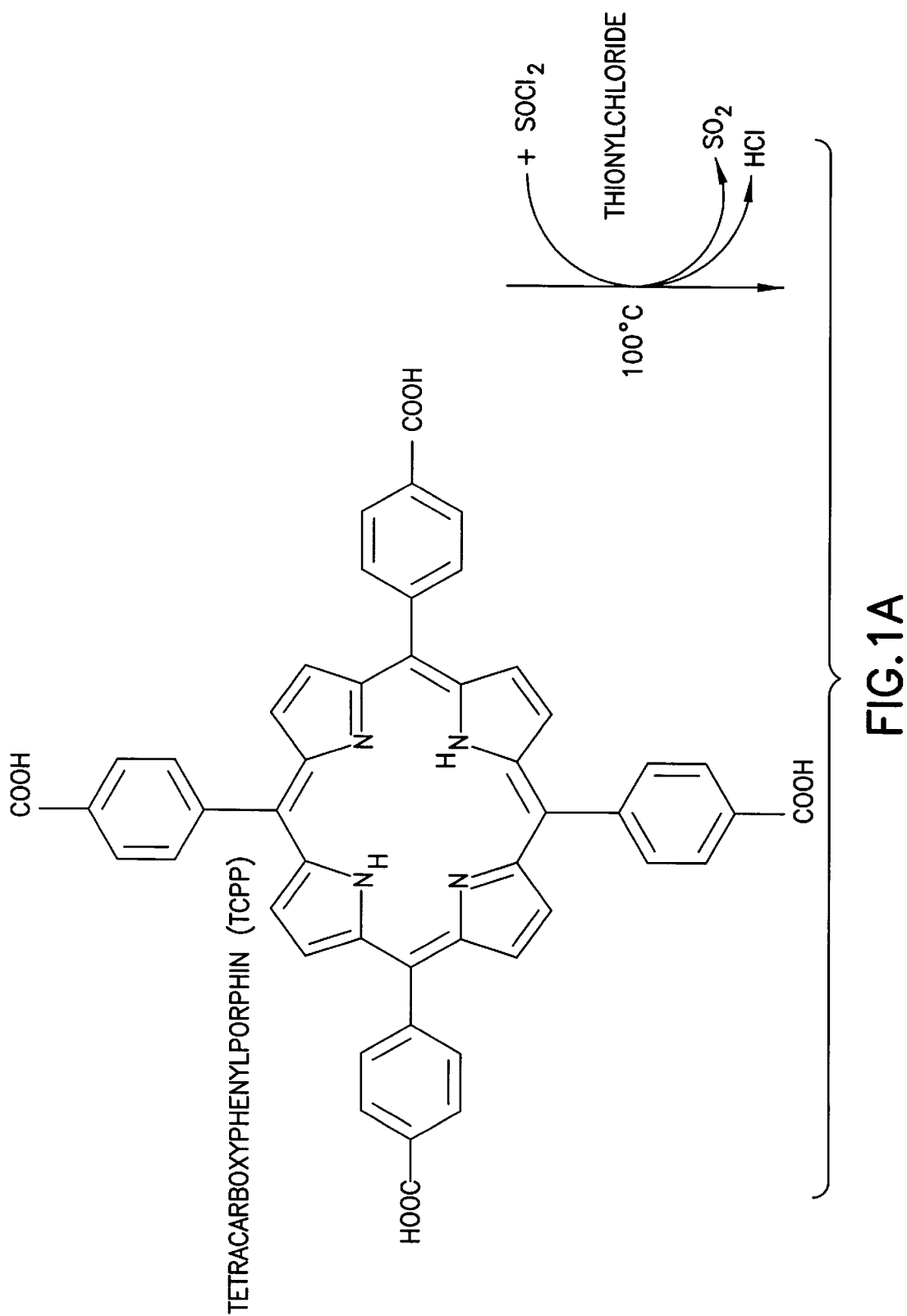
FIGS. 1A–1D shows the preparation of polyether-including chlorins and bacteriochlorins according to the invention. For this purpose, TCPP is reacted with thionyl chloride to convert the carboxylic acid groups of TCPP into the acid chloride form. This is followed by the binding of 4 aminoPEG and the reduction with toluenesulfonic acid hydrazide, so as to obtain a polyether-including chlorin and bacteriochlorin.
Figure 1B:
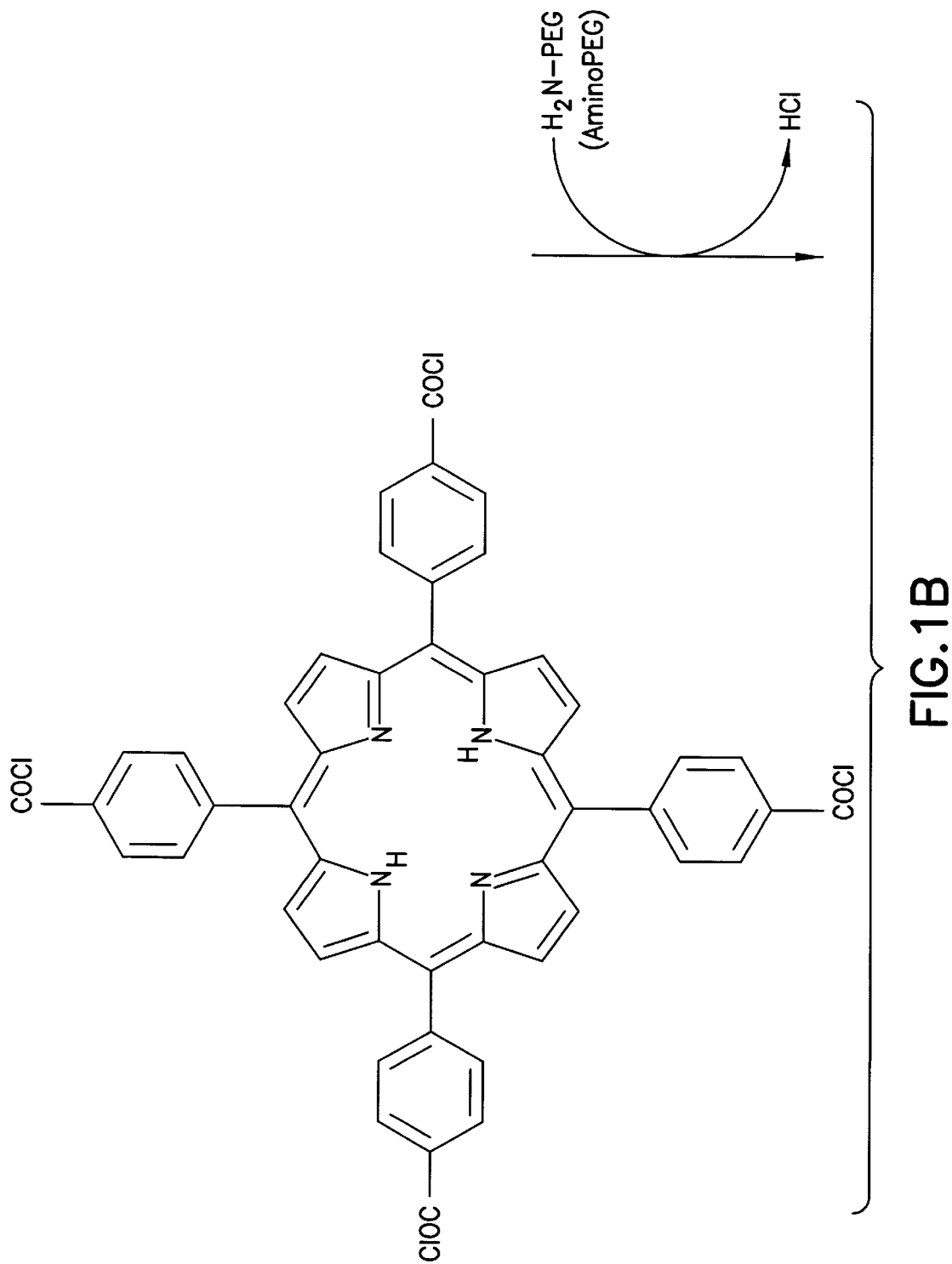
Figure 1C:
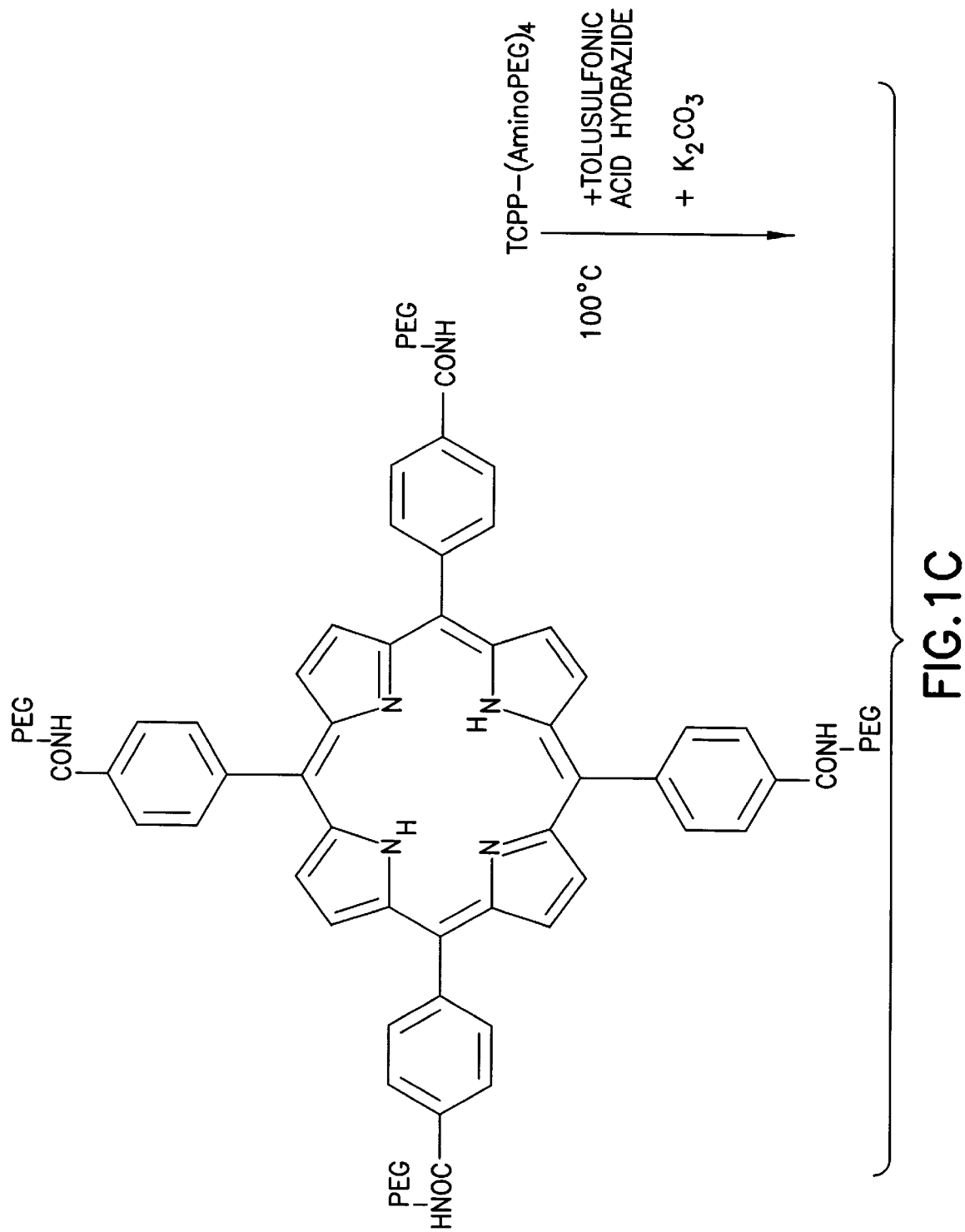
Figure 1D:
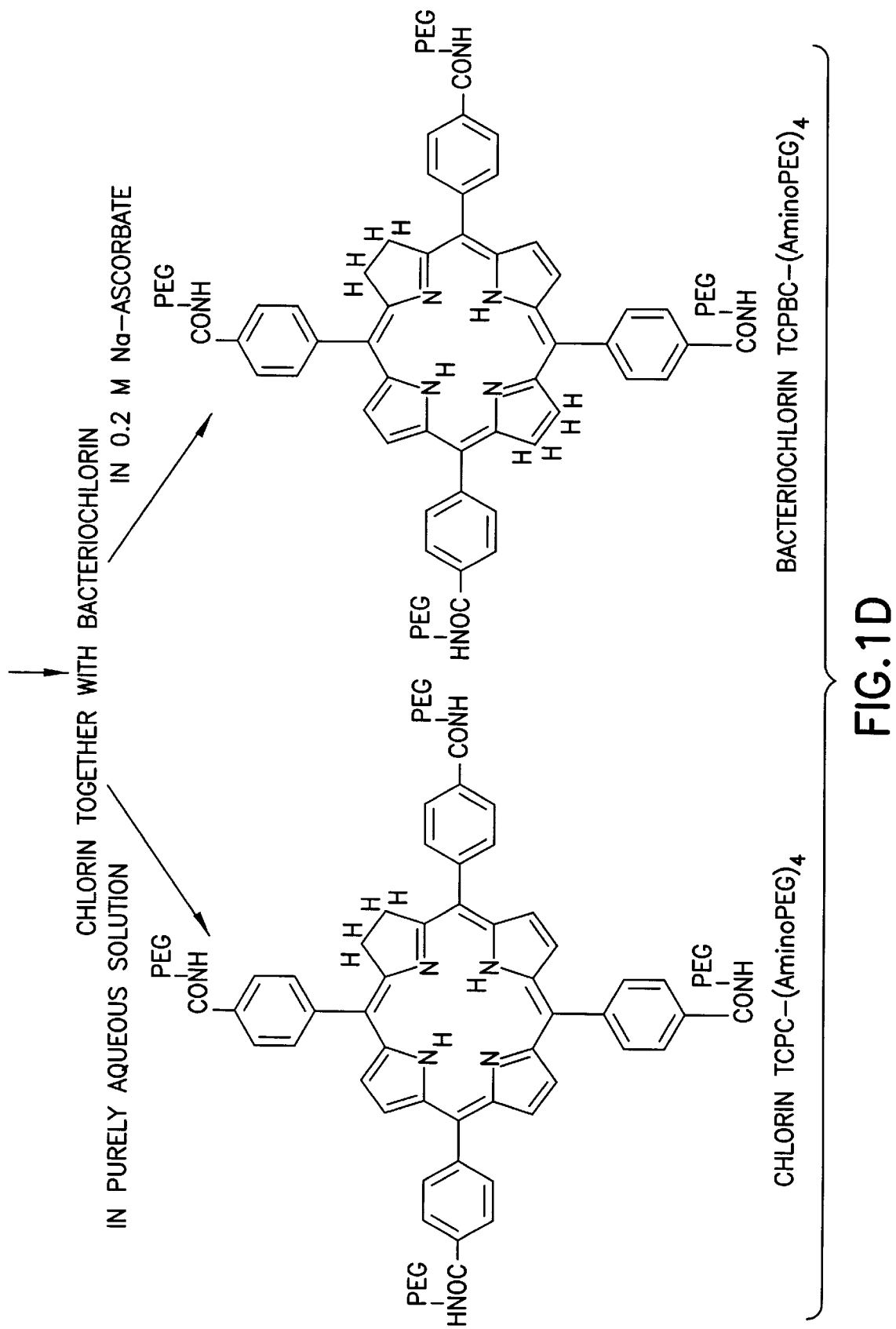

The preparation is shown in FIGS. 1A–1D.

1. Preparation of the acid chloride of TCPP:

40 mg of p-tetracarboxyphenylporphin were added to a 50 ml round bottom flask with NS 29 and admixed with 5 ml thionylchloride ($SOCl_2$). After attaching a reflux cooler, the mixture was heated in a silicon oil bath to about 100° C., an intensely green solution forming after a short time already. For completing the reaction, the mixture was refluxed for about 30 minutes. Thereafter, the excess $SOCl_2$ was removed in a rotary evaporator.

2. Reaction of the acid chloride of TCPP with amino-Ω-methoxypolyethylene glycol (aminoPEG)

1 g aminoPEG, dissolved with slight heating in 10 ml 1,4-dioxan, and about 1 ml of ethylene triamine were added to the dry residue of the above acid chloride and heated to 130° C. for 30 minutes, an intensely red solution forming. TCPP-(aminoPEG)$_4$ was obtained.

3. Reaction of the TCPP-(aminoPEG)$_4$ to form the corresponding chlorin and bacteriochlorin After cooling the TCPP-(aminoPEG)$_4$ solution, it was converted into a 150 ml three-neck flask (sulfonation flask having 2 NS 14.5 and one NS 29 cuts) and about 0.5 g $K_2CO_3$ as well as 100 mg of toluenesulfonic acid hydrazide (TSH) were added. The reaction vessel was provided with a reflux cooler and a gas inlet capillary. Before the reaction mixture was heated, rinsing with nitrogen took place for about 20 minutes to displace the air.

Thereafter, the reaction solution was heated to a temperature of about 100° C. After about 1.5 hours, 100 mg of TSH were added again through the third side neck. This addition was repeated after another 1.5 hours. After a total reaction time of about 6 hours, the reaction into chlorin (TCPC) was completed, part of the TCPP-(aminoPEG)$_4$ having been converted into the bacteriochlorin form (TCPBC). The formation of TCPC and TCPBC may be observed by occasional sampling and the spectroscopic investigations thereof.

4. Purification and conversion, respectively, into pure chlorin

After cooling, the reaction solution was added to 1 l of bidistilled water for providing chlorin and the unwanted accompanying substances were separated by ultrafiltration (Amicon YM 10). The process was carried out in weakly reducing medium (0.1 M Na ascorbate) to obtain the bacteriochlorin.

What is claimed is:

1. A process for the preparation of polyether-including chlorins and/or bacteriochlorins, comprising the following steps:

(a) bonding a polyether to a porphyrin and (b) reacting the polyether-including porphyrin with a reducing agent.

2. The process according to claim 1, wherein the porphyrin has at least one acid group.

3. The process according to claim 2, wherein the porphyrin is o-, m- and/or p- tetracarboxyphenlyporphin and o-, m- and/or p- tetrasulfophenylporphin, respectively.

4. The process according to claim 1, wherein the polyether has a molecular weight of 100 to 20,000 daltons.

5. The process according to claim 1, wherein the polyether is a polyethylene glycol.

6. The process according to claim 1, wherein several polyethers are bonded to the porphyrin.

7. The process according to claim 1, wherein reduction takes place by means of hydrazide.

8. The process according to claim 1, wherein steps (a) and (b) are carried out in an organic polar solvent.

9. The process according to claim 1, wherein step (b) is followed by an isolation step.

10. A polyether-including chlorin or bacteriochlorin, of the formula:

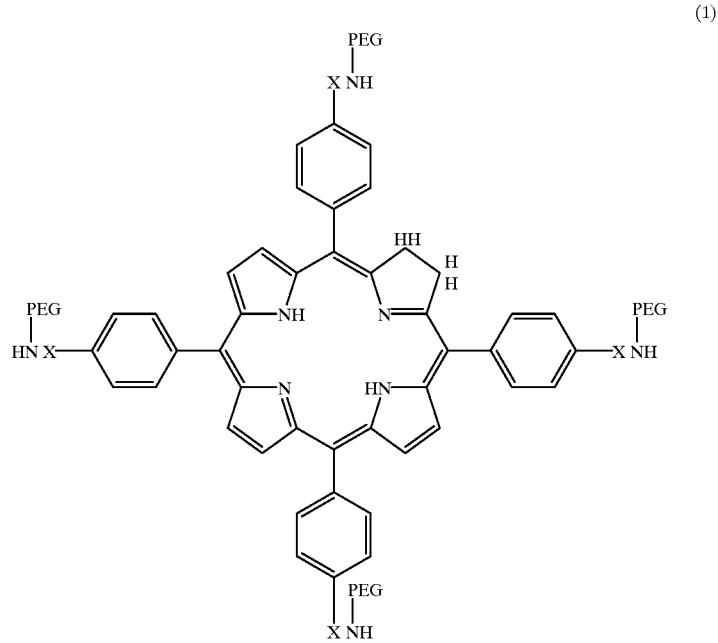

(1)

or

-continued

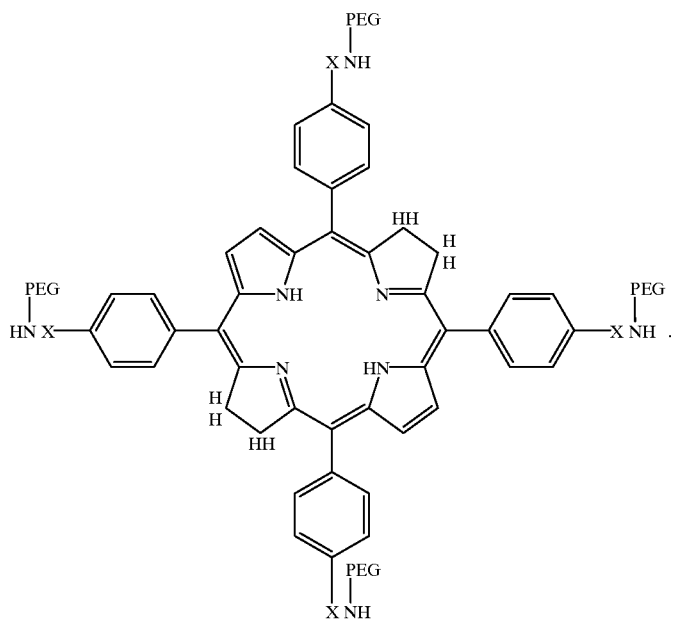

(2)

11. A method of photodynamic therapy, comprising the use of a polyether-including chlorin or bacteriochlorin, formed by a process comprising the steps of:
    (a) bonding a polyether to a porphyrin and
    (b) reacting the polyether-including porphyrin with a reducing agent.

12. A method of photodynamic therapy, comprising the use of a polyether-including chlorin or bacteriochlorin, of the formula:

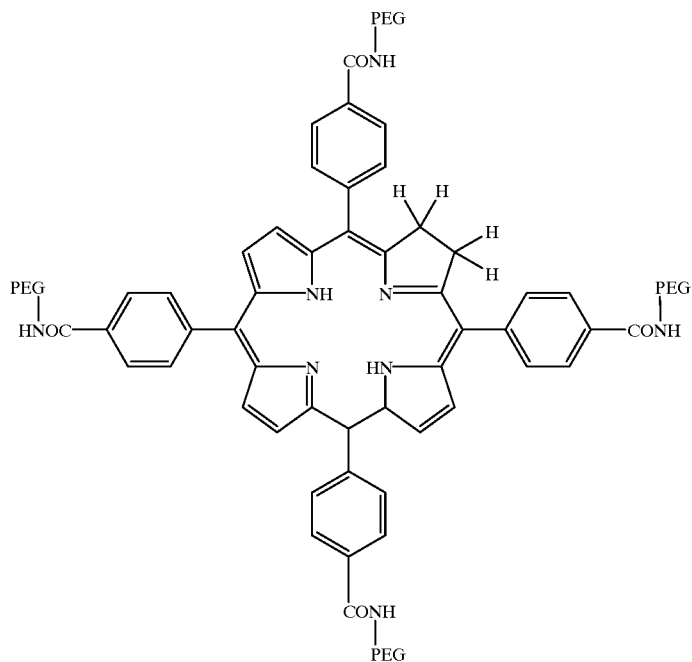

(I)[1]

or

-continued
(II)
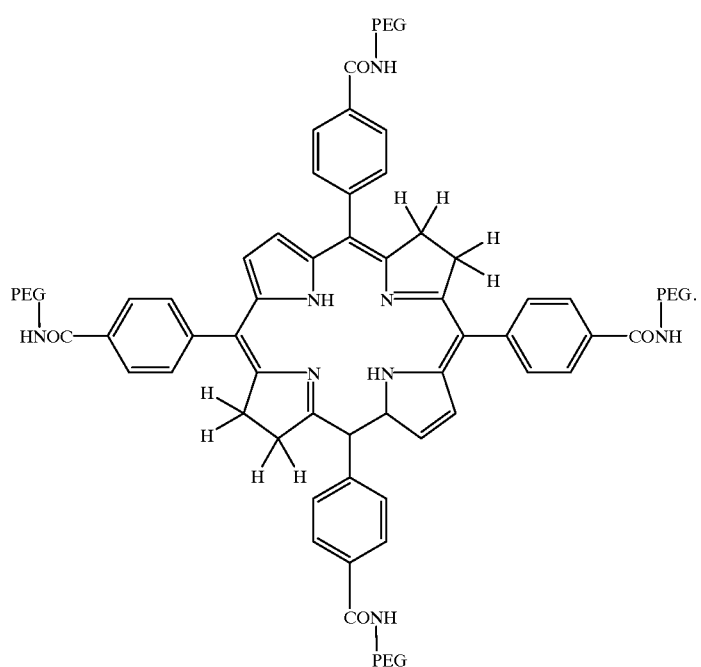
* * * * *